United States Patent [19]
Rottermann et al.

[11] Patent Number: 5,988,029
[45] Date of Patent: Nov. 23, 1999

[54] HEIGHT-ADJUSTABLE TABLE FOR A MICROTOME

[75] Inventors: Bernd Rottermann, Birkenau; Manfred Berleth, Eppelheim, both of Germany

[73] Assignee: Microm Laborgerate GmbH, Germany

[21] Appl. No.: 08/939,173

[22] Filed: Sep. 29, 1997

[30] Foreign Application Priority Data

Sep. 30, 1996 [DE] Germany .................. 296 16 881

[51] Int. Cl.⁶ .................. G01N 1/06; B26D 7/18
[52] U.S. Cl. .................. 83/100; 83/168; 83/915.5; 83/177; 108/138; 269/27
[58] Field of Search .................. 83/100, 168, 169, 83/177, 915.5, 170, 171; 108/20, 138, 143, 144.11; 248/429, 297.11, 298.1; 254/122; 269/903, 20, 27, 312

[56] References Cited

U.S. PATENT DOCUMENTS

| | | | |
|---|---|---|---|
| 3,191,476 | 6/1965 | McCormick et al. | 83/915.5 X |
| 3,204,424 | 9/1965 | McCormick et al. | 83/915.5 X |
| 3,491,638 | 1/1970 | Idlis | 83/915.5 X |
| 3,603,189 | 9/1971 | Stachl | 83/915.5 X |
| 3,611,875 | 10/1971 | Wistedt | 83/915.5 X |
| 4,060,440 | 11/1977 | Behme et al. | 83/915.5 X |
| 4,566,741 | 1/1986 | Eriksson et al. | 108/138 X |
| 4,703,700 | 11/1987 | Sema | 108/11 |
| 4,714,028 | 12/1987 | Uredat-Neuhoff | 108/144 |
| 4,979,376 | 12/1990 | Biehl et al. | 83/915.5 X |
| 5,161,446 | 11/1992 | Holbl et al. | 83/915.5 X |
| 5,255,585 | 10/1993 | Gordon | 83/100 |

FOREIGN PATENT DOCUMENTS

0085420 A1  1/1983  European Pat. Off. .

*Primary Examiner*—Rinaldi I. Rada
*Assistant Examiner*—Boyer Ashley

[57] ABSTRACT

The combination of a table and a table-type microtome has a base having an internal volume and a linear guide. A seating device is movably mounted on the base. The seating device is movable along the linear guide. A drive causes movement of the seating device relative to the base along the linear guide for height adjustment. A table-type microtome is arranged on the seating device. At least one appliance for the table-type microtome is arranged in the internal volume of the base and is operatingly connected to the table-type microtome.

8 Claims, 2 Drawing Sheets

HEIGHT-ADJUSTABLE TABLE FOR A MICROTOME

BACKGROUND OF THE INVENTION

1. Field of the Invention

This invention relates to a table for a microtome, and more particularly, to a table for a microtome having a base and a height adjustable seating device on which the microtome is placed.

2. Discussion of Relevant Art

Such tables have long been known in the state of the art in the form of units integrated into the microtome for seating the microtome, particularly for cryostatic microtomes where the microtome is located in a low-temperature chamber.

Such a table is known, for example, from U.S. Pat. No. 4,548,051. The table has a drive for height adjustment, constructed as follows. Four threaded sleeves are provided on the outer edges of the rectangular seating device, each engaged by a respective threaded spindle. The four threaded spindles can be turned, via a mechanism, by a motor in the base. The height of the receiving device can be vertically adjusted by means of the sleeves when the spindles are turned.

In another embodiment in the above referenced patent, the drive is constructed as follows. Rotatably mounted gear wheels are provided at the corners of the seating device and respectively engage with a rack fastened in the base. Height adjustment takes place by rotation of the gearwheels. The gearwheels are driven via a mechanism by a hand crank in the seating device.

In a third embodiment in the above referenced patent, not described in detail, the seating device is mounted by means of at least two height-adjustable gas pressure springs.

In the tables described above, the drives have a double function. On the one hand, they serve to adjustment the height of the seating device; and on the other hand, they serve for mounting the seating device. The drive therefore engages the seating device at at least two points, or better still at four points, to ensure stable mounting.

SUMMARY OF THE INVENTION

The object of the present invention is to provide a table of the kind described that is simple to produce and in which the height of the seating device may be adjusted in a relatively simple manner.

This object is attained according to the invention by a table for a microtome including a base, a seating device mounted height adjustably on the base and arranged to carry the microtome. It also includes a drive for adjusting the height of the seating device. The seating device is mounted displaceably on the base independently of the drive.

An important feature of the invention is that the seating device is mounted displaceably on the base, independently of the drive for adjusting the height of the seating device and the microtome.

An important advantage of such an arrangement is that the drive is no longer required for mounting the seating device. Therefore, it is sufficient for the drive to engage the seating device at only one place, without losing stability while guiding the seating device. The drive can be very simply provided in the form of a single, inexpensive standard drive, such as, for example, an electrically driven cylinder that operates under tension or pressure.

The mounting can be arranged in various ways. For example, the seating device can be mounted for vertical displacement, so that the seating device can move vertically up and down as in the conventional equipment. In a particularly advantageous embodiment, for certain uses, the seating device is mounted on a plane of the base that is inclined relative to the floor.

Various possibilities for mounting the seating device on the inclined plane may be considered. For example, the seating device can be guided on rods that are fixedly connected to the base. Also, the seating device may be guided by means of a needle bearing located in a guide track with a closed slot.

Due to mounting the seating device displaceably on the inclined plane, less force is required to raise the seating device and the microtome than for conventional tables. Consequently the drive can have smaller dimensions. Additionally, due to the inclined plane, the back side of the base is relatively tall, and does not become shorter even when the seating device is lowered. Thus, large additional appliances or components may be fitted at the back side of the base without any problems. This will be described in greater detail below.

An electrically driven cylinder is used as a drive for the height adjustment of the seating device. It is fastened to the seating device and to the base, and is particularly advantageous if it operates essentially in the direction of the inclined plane and displaces the seating device on the inclined plane. The electrically driven cylinder can either work on pressure, so that it pushes the seating device up the inclined plane to raise the microtome, or can work on tension and pull the seating device up the inclined plane to raise the microtome. Many other possibilities exist, such as an electric motor located in the base and winding a steel cable attached to the seating device on a drum, thus pulling the seating device up the inclined plane.

In particular, the table can be constructed so that it is made for small, table-type cryostatic microtomes. Such table-type cryostatic microtomes can be built to save space, so that possible additional functions, such as a disinfecting device for the microtome located in the cryostatic microtome, can be fitted outside the cryostatic microtome. Since the arrangement of the whole cryostatic microtome with its auxiliary functions as a closed unit on the table is worth striving for, it is in addition possible, and particularly advantageous, to provide appliances in the base of the table that cooperate with the microtome. For example, such appliances can be a suction device to suck out sectioning waste. The especially tall height at the rear side of the base, due to the inclined plane, is particularly advantageous for arranging the appliances in the base. Since this height is not reduced when the seating device is lowered, relatively tall appliances may be fitted at the rear side of the base.

BRIEF DESCRIPTION OF THE DRAWINGS

Preferred embodiments of the invention will now be described, taken together with the drawings, in which.

DETAILED DESCRIPTION OF PREFERRED EMBODIMENTS

Figure 1:
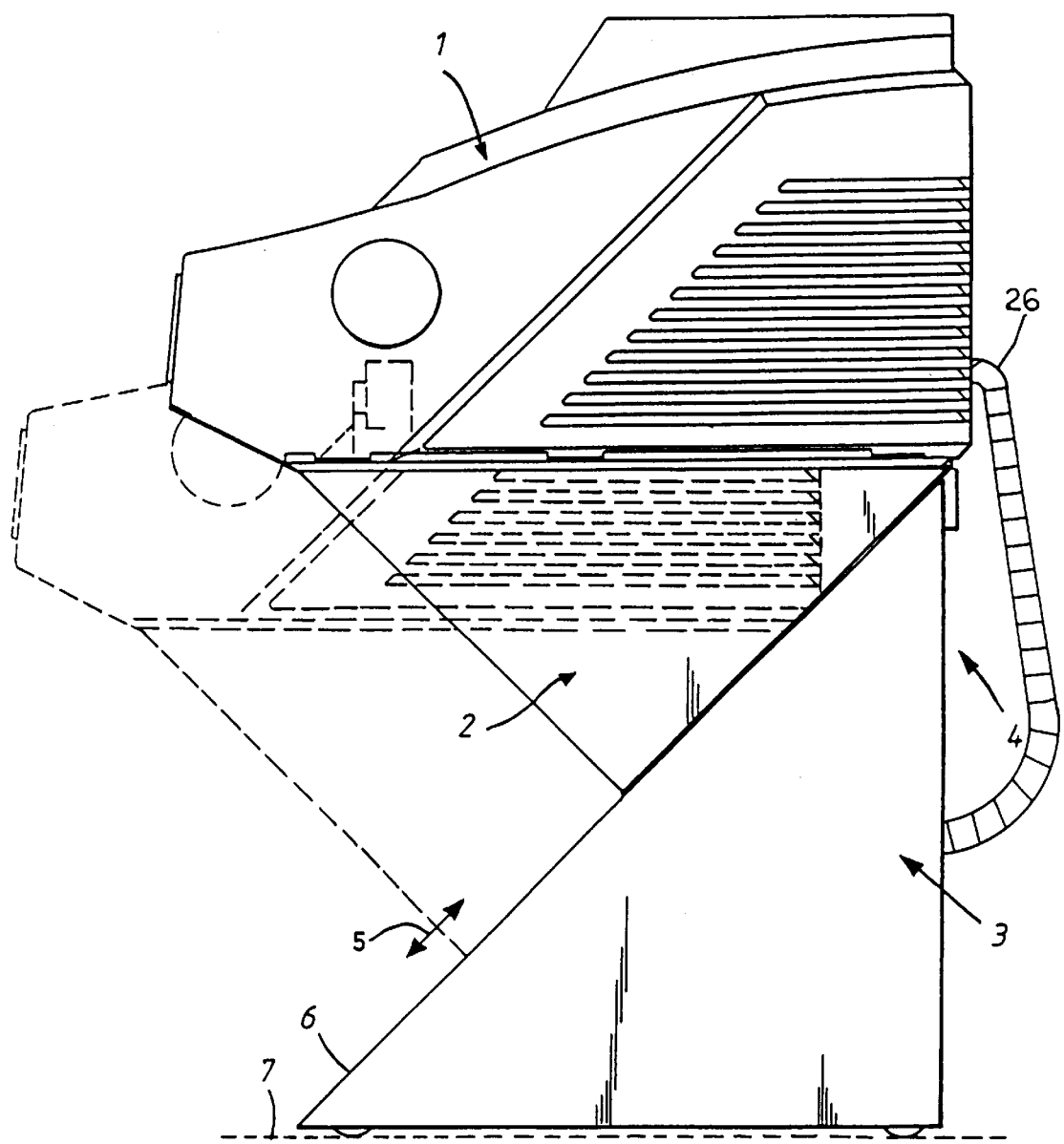
FIG. 1 shows a side view of a table according to the invention, with a cryostatic microtome located on it.

FIG. 1 shows a table (4) according to the invention for a cryostatic microtome (1), wherein the table (4) is constructed from a base (3), and a seating device (2) on which the cryostatic microtome (1) may be placed. The seating device (2) is height adjustable relative to the base. As may be seen from FIG. 1, the seating device (2) is mounted on a plane (6) of the base (3), and is displaceable in the direction of the arrow (5) for adjusting the height. The plane (6) is inclined relative to the floor (7).

The drawing in full lines shows the seating device (2) and the cryostatic microtome (1) in the raised state, while the drawing in dashed lines shows these components in the lowered state.

The angle between the floor (7) and the inclined plane (6) can vary widely, in a range between 0° and 90°. The illustration shows an angle of 45° between the floor and the inclined plane. If the angle is smaller, the force required to raise the seating device (2) is reduced. The horizontal movement necessary to lower the seating device by a defined amount is, of course, then increased. The opposite is true when the angle is increased.

Further details of the invention are explained with reference to FIG. 2, in which the table (4) according to the invention is shown in section. The drawing relates only to essential elements of the table. For example, electronic components, connecting elements and the like are omitted for the sake of simplicity. The construction of the table (4) is as follows. The base (3) consists essentially of two parallel side sheets (8), only one of which is shown in this sectional view. The side sheets (8) are welded together by means of the struts (9, 10, 11). A respective runner tube (12) is screwed to the inward-facing side of each side sheet (8); and two guide bars (13a, 13b) extend in each runner tube (12). Each guide bar (13a, 13b) receives and guides a needle bearing (14a, 14b) without a corresponding inner ring. The runner tubes (12) and the guide bars (13a, 13b) have slots (15a, 15b) to receive the needle bearings (14a, 14b). In addition, rollers (16a, 16b) are fastened to the underside of the side sheets (8), and facilitate moving the base (3).

The seating device (2) has two parallel directed side sheets (17), only one of which is shown here. The side sheets are spaced apart and welded together by means of angle bars (18a, 18b, 18c). A metal plate (19) is screwed to the side sheets (17) of the seating device (2), and receives two hardened cylinder rods, not shown in detail here, which extend into the needle bearings (14a, 14b). The seating device (2) is thereby movably guided on the base (3) by means of a needle bearing (14a, 14b) located in a guide bar (13a, 13b) with a closed slot (15a, 15b).

An electrically driven cylinder fastened to the seating device (2) and to the base (3) acts as the drive (21) for adjusting the height of the seating device (2). A holder (22) is screwed firmly to the base (3) to receive the drive on the base (3), while a corresponding holder (20) is fastened to the seating device (2) to attach the drive. As has already been described, the seating device mounting takes place by means of the needle bearings (14a, 14b), so that the seating device (2) is displaceably mounted on the base (3) for adjusting the height, independently of the drive (21).

Figure 2:
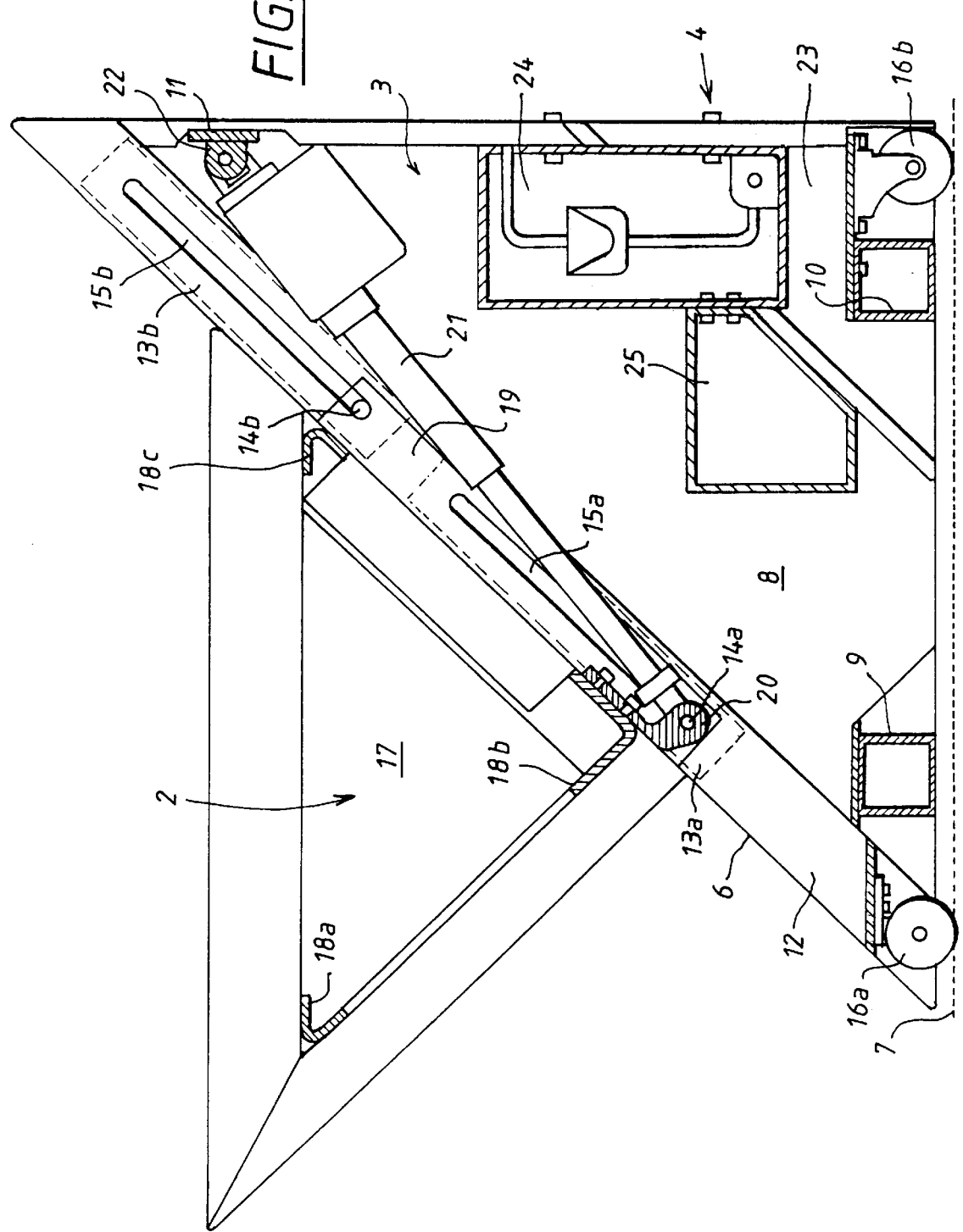
FIG. 2 shows a section of a table according to the invention, according to FIG. 1, without a cryostatic microtome located on it.

The cryostatic microtome shown in FIGS. 1 and 2 is a relatively small table appliance, which does not have all the possible functions provided. Optional appliances can be provided in the base (3) and work with the microtome in the cryostatic microtome (1). For example, the appliances can be a suction device (24) for sucking away sectioning waste, or a disinfecting device (25) for disinfecting the microtome. The appliances can then be connected to the cryostatic microtome (1) by flexible tubes (25). The great height of the base (3) in the rear region, which is about the maximum raised height of the seating device (2), is particularly advantageous for receiving such appliances. This maximum height is not reduced when the seating device (2) is lowered, as is normally the case for conventional tables.

It should be understood that the invention is not limited to the embodiment shown here, but includes all similar tables that can be manufactured in a similar form.

We claim:

1. The combination of a table and a table-type microtome, the combination comprising:
    said table including:
        a table base having an internal volume and comprising at least one linear guide;
        a table seating device movably mounted on said base, said seating device being movable along said at least one linear guide;
        a table drive supported by said base and causing a movement of said seating device relative to said base along said at least one linear guide for height adjustment of said seating device; and
        at least one appliance for said table-type microtome mounted within the internal volume of said table base and being operatingly connected to said table-type microtome:
    said table-type microtome including:
        a microtome base being arranged on said seating device:
        a blade and a specimen holder mounted to said microtome base:
    wherein a portion of said at least one appliance, that is operatingly connected to said table-type microtome, is mounted to said table-type microtome and configured to move with the table-type microtome and the seating device when the height of the seating device is adjusted.

2. The combination according to claim 1, wherein said base includes an inclined plane on which said seating device is displaceably mounted.

3. The combination according to claim 1, wherein said at least one appliance comprises a suction device for sucking away cutting waste.

4. The combination according to claim 1, wherein said at least one appliance comprises a disinfectant device for disinfecting said microtome.

5. The combination according to claim 1, wherein said drive (21) comprises an electrically driven cylinder fastened to said seating device (2) and to said base (3) for height adjustment of said seating device (2).

6. The combination according to claim 1, further comprising a plurality of needle bearings (14a, 14b) arranged in a guide bar (13a, 13b) with a closed slot (15a, 15b) associated with said base (3) for movably guiding said seating device (2).

7. The combination according to claim 1, further comprising at least one flexible tubing for operatingly connecting said at least one appliance to said table-type microtome.

8. The combination of a table and a table-type microtome, the combination comprising:
    said table including:
        a table base having two parallel trianglur side sheets;
        at least one appliance for said table-type microtome arranged in said table base between said side sheets, said side sheets defining an inclined surface;
        a drive supported by said table base and causing movement of said table seating device relative to said base along said guides for height adjustment:

said table base further having linear guides along said inclined surface;
a table seating device movably mounted on said base, said table seating device being moveable along said linear guides; and
said table-type microtome including:
a microtome base being arranged on said table seating device;
a blade and a specimen holder mounted to said microtome base;

wherein said at least one appliance being operatingly connected to said table-type microtome such that a portion of said at least one appliance, that is operatingly connected to said table-type microtome, is mounted to said table-type microtome and configured to move with the table-type microtome and the seating device when the height of the seating device is adjusted.

* * * * *